United States Patent [19]

Hart

[11] Patent Number: 5,584,845
[45] Date of Patent: Dec. 17, 1996

[54] SURGICAL SCISSOR BLADE AND METHOD FOR MAKING THE SAME

[75] Inventor: Rickey D. Hart, Plainville, Mass.

[73] Assignee: Innovasive Devices, Inc., Marlborough, Mass.

[21] Appl. No.: 292,370

[22] Filed: Aug. 18, 1994

[51] Int. Cl.[6] .................................................. A61B 17/32
[52] U.S. Cl. ................................. 606/174; 606/206
[58] Field of Search ............................ 606/206, 174; 30/194, 208, 212, 213, 214, 286, 287, 288

[56] References Cited

U.S. PATENT DOCUMENTS

| 140,292 | 6/1873 | McWilliams | 30/234 |
|---|---|---|---|
| 4,369,787 | 1/1983 | Lasner et al. | 606/174 |
| 4,755,237 | 7/1988 | Lemelson | 148/152 |
| 5,147,356 | 9/1992 | Bhatta | 606/174 |
| 5,190,102 | 3/1993 | Arterbury et al. | 166/228 |

OTHER PUBLICATIONS

John A. Vaccari, "Take A New Look At Metal Injection Molding", American Machinist, Dec. 1988, pp. 45–48.

*Primary Examiner*—Michael Powell Buiz
*Assistant Examiner*—Mark S. Leonardo
*Attorney, Agent, or Firm*—Pandiscio & Pandiscio

[57] ABSTRACT

A novel surgical scissor blade having a sharp shearing edge and comprising an injection molded powdered metal, and a method for making the same.

11 Claims, 4 Drawing Sheets

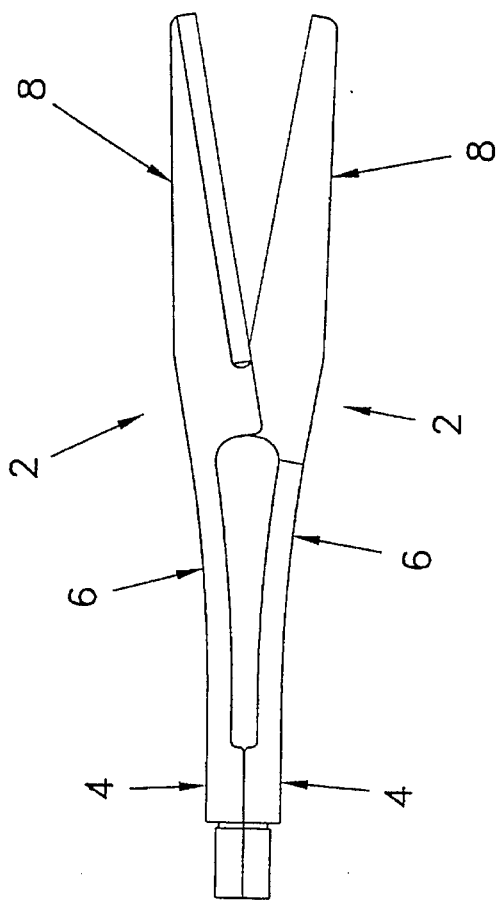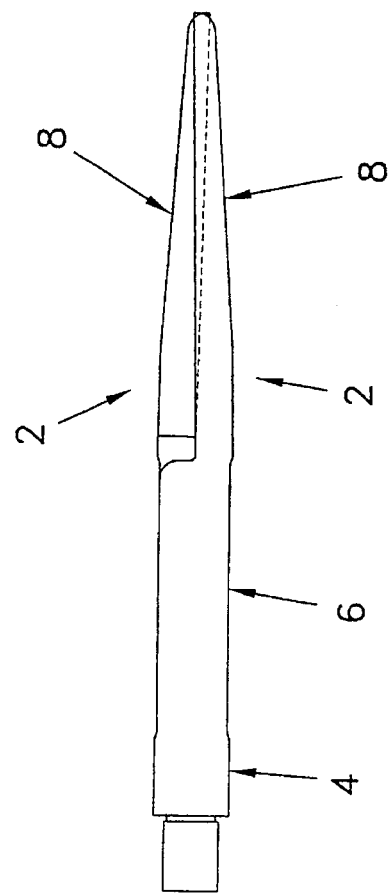

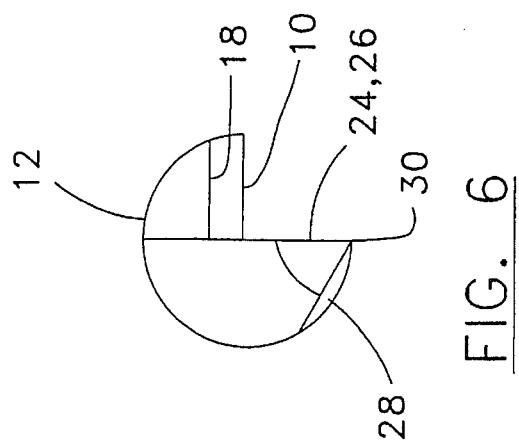
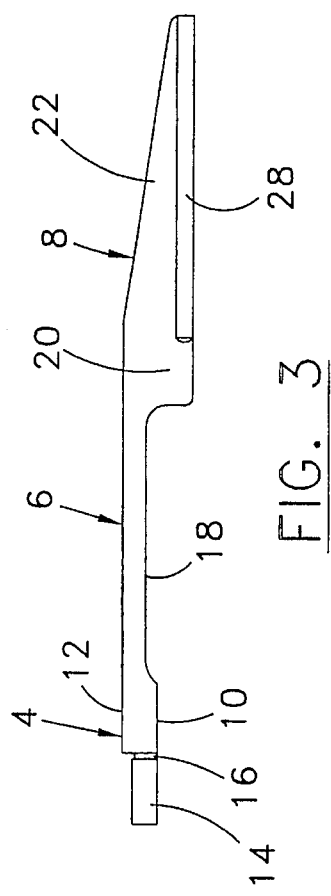
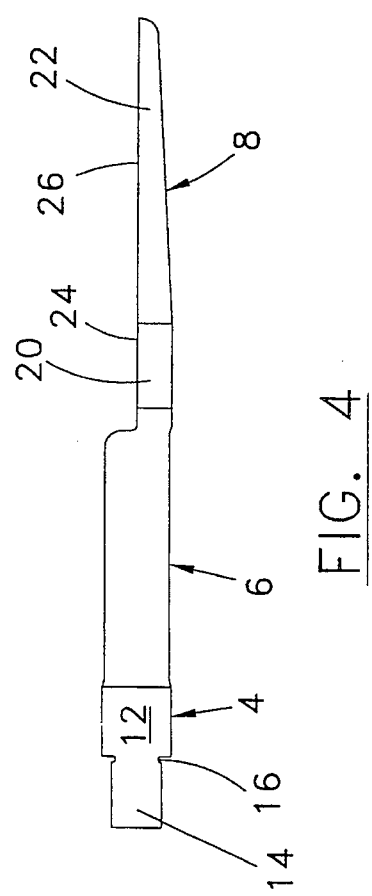
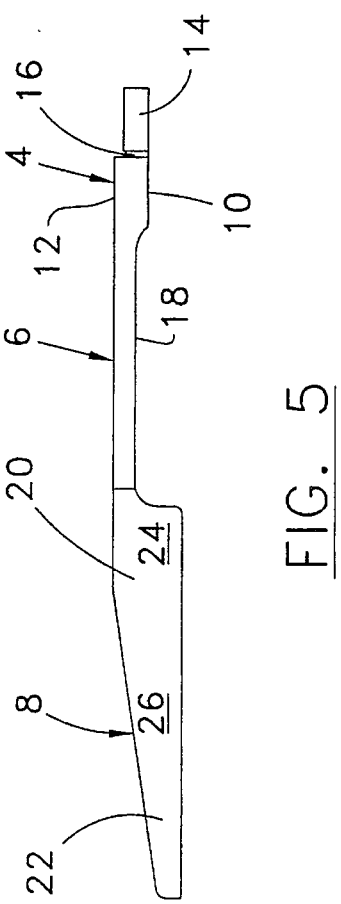

SURGICAL SCISSOR BLADE AND METHOD FOR MAKING THE SAME

FIELD OF THE INVENTION

This invention relates to surgical cutting instruments in general, and more particularly to scissor blades for use in surgical scissors.

BACKGROUND OF THE INVENTION

Endoscopic surgical procedures, such as arthroscopic and laparoscopic surgeries, continue to displace conventional open surgical procedures in many situations. A wide variety of surgical instruments have been developed for use in such arthroscopic and laparoscopic surgical procedures, including surgical scissors for use in cutting remotely positioned bodily tissue and other matter.

Endoscopic surgical scissors are well known in the art. In general, such scissors comprise a pair of opposing blade members adapted to open and close relative to one another, and a handle mechanism for supporting the blade members and causing them to open and close. The blade members are typically located at the distal end of the handle member, and various cutting edges, serrations or other features are provided on the blade members so as to enable them to cut the desired tissue as they open and close. The handle member typically includes an elongated midsection, whereby the cutting blades can be positioned deep within the body at a remote surgical site while the grasping portion of the handle mechanism remains outside the body for convenient engagement by the surgeon. In general, the length of the handle member's elongated midsection is determined by the depth of the surgical site, while the cross-sectional dimensions of the handle member's elongated midsection are limited by the size of the access portal leading to the interior surgical site.

Surgical scissor blades must generally be made of high strength, ductile metal materials such as stainless steels, titanium-aluminum alloys and the like so that they will retain their sharpness during use and withstand repeated high temperature sterilizations. Typically, one side of the scissor blade is provided with a sharp shearing edge which is formed by a large included angle so that the scissor blade will have the requisite structural strength and durability. The shearing edge is ground sharp so as to provide a quick, precise, and accurate cut.

Prior art surgical scissor blades have typically been manufactured by conventional stamping, forging or machining methods. More particularly, metal rod or bar stock is generally first formed into rough blanks of approximately the required size and shape. A sharp shearing edge is then carefully ground onto at least one side of the blank. This grinding step is required in order to achieve the high degree of sharpness required for surgical applications. Unfortunately, during grinding, burrs are invariably formed on the shearing edge of the scissor blade as the grinding wheel works away at the ductile metal blank. These burrs must then be carefully removed from the blade's shearing edge before the scissor blade can be used in a surgical procedure. Furthermore, after the aforementioned grinding and deburring steps, the blade must also typically be polished to the desired surface finish before use.

Burr removal is a relatively costly manufacturing step. However, it is also an absolutely necessary manufacturing step for all prior art surgical scissor blades, since any burrs left on a surgical scissor blade during manufacture could break free from the blade during surgery and thereafter become lodged in the patient's body. Thus, it is absolutely essential that all burrs, even microscopic burrs, be removed from surgical scissor blades prior to their use in surgery.

Unfortunately, the deburring process requires significant additional labor, thus slowing down the manufacturing operation and increasing cost. Furthermore, the deburring process also tends to increase scrap, since a significant amount of additional metal must generally be removed from the blade during manufacture in order to achieve a sharp shearing edge that is burr free. When the scissor blades are being formed out of relatively exotic metal alloys, this increased scrap rate can significantly increase the overall cost of producing the scissor blades.

In some surgical procedures, curved scissor blades, scissor blades with non-planar profiles, or scissor blades with customized profiles may be required. Such non-standard scissor blade configurations are generally more difficult to produce using conventional manufacturing techniques. In order to produce such non-standard scissor blade shapes using prior art manufacturing techniques, custom grinding and machining of the metal blank must frequently be performed. These additional steps tend to further increase the cost of producing the scissor blades.

In addition to the foregoing, with certain scissor designs, the surgical scissor blades must also be resilient. More particularly, in U.S. Pat. No. 5,334,198, issued Aug. 2, 1994 to Rickey D. Hart et al., surgical scissors are disclosed which comprise a pair of resilient scissor blade members. The blade members are formed so that they are in their open position when they are in their normal, relaxed state, but are capable of being elastically deformed so as to assume their closed position. It has been found that forming such resilient scissor blade members with conventional manufacturing methods can add certain complexitites and costs to the manufacturing process.

Finally, as stated above, surgical scissors are employed in many different surgical procedures currently being performed by the medical profession. The high cost of manufacturing these cutting instruments adds significantly to the overall high cost of health care in the United States, particularly in those circumstances where the surgical scissors are designed to be disposable so that they are discarded after being used in a single surgical procedure.

OBJECTS OF THE INVENTION

Accordingly, one object of the present invention is to provide a new surgical scissor blade which includes a sharp shearing edge suitable for cutting tissue.

Another object of the present invention is to provide a new surgical scissor blade which includes a sharp shearing edge, wherein the sharp shearing edge is created on the scissor blade without forming any burrs thereon during manufacture.

Yet another object of the present invention is to provide a new surgical scissor blade which includes a sharp shearing edge, wherein the sharp shearing edge is created on the scissor blade without the need to further sharpen or polish the blade.

And another object of the present invention is to provide an improved surgical scissor blade which includes a sharp shearing edge and which is resilient.

Still another object of the present invention is to provide a new method for manufacturing surgical blades having complex shapes.

And another object of the present invention is to provide a new method for manufacturing a surgical scissor blade which has a low scrap rate.

Yet another object of the present invention is to provide a new method for manufacturing surgical scissor blades which reduces the cost of manufacture.

Still another object of the present invention is to provide a new method for manufacturing surgical scissor blades which are resilient.

SUMMARY OF THE INVENTION

These and other objects are achieved by the present invention, which comprises a novel surgical scissor blade and a method for making the same, wherein the scissor blade includes a sharp shearing edge and is formed out of an injection molded powdered metal. The injection molded powdered metal blade of the present invention naturally possesses a completely burrless shearing edge of unexpected sharpness and significantly improved cutting performance, as compared to prior art scissor blades formed using conventional manufacturing techniques. Furthermore, when the scissor blades of the present invention are assembled, they exhibit superior spring properties and unexpected fatigue strength compared to conventional scissor blades.

The surgical scissor blade of the present invention is manufactured by mixing a suitable powdered metal with a binder and selected additives, adding this mixture to the hopper of a conventional injection molding machine, and then injecting the mixture into a mold having a cavity formed in the size and shape of the desired scissor blade. The molded part is then removed from the mold after a short cooling period. This molded part has the sharp shearing edge needed for cutting tissue, without any burrs thereon. At this point the molded blade, frequently referred to as "green", may be stored for some period of time, or it may be placed directly into a debinderizing chamber for debinderizing.

The debinderizing process subjects the green blade to an elevated temperature, under a vacuum, for a predetermined period of time, so as to burn off the binder and additives from the molded part. After debinderizing, the green blade is then placed in a second chamber where it is sintered at a second elevated temperature, in a non-oxidizing atmosphere. This causes the metal particles in the molded blade to strongly adhere to one another so as to give the blade its required structural integrity. Once sintered, the blade may then have additional forming or machining processes performed to it so as to add specific features to the blade which are not obtainable by injection molding alone. Finally, the sintered blade is heat-tempered so as to harden it and provide the blade with the desired degree of resiliency.

Various scissor blade sizes and shapes can be formed in this manner, including straight blades, curved blades, hooked blades, serrated blades, etc., all including the sharp shearing edge required for cutting tissue. Miniature versions of all of the foregoing shapes can also be formed using an appropriate mold.

The completed scissor blade may then be joined with a matching scissor blade for assembly into a pair of surgical scissors.

At no time during the aforementioned manufacturing process is there ever a need to grind or sharpen the blade's shearing edge. Furthermore, no burr is ever created during the fabrication of the blade. Consequently, no deburring or polishing step need ever be done to the blade prior to its use.

BRIEF DESCRIPTION OF THE DRAWINGS

These and other objects and features of the present invention will be more fully disclosed or rendered obvious in the following detailed description of the preferred embodiment of the invention, which is to be considered together with the accompanying drawings where like numbers refer to like parts and further wherein:

FIG. 1 is a right side view of a pair of surgical scissors formed in accordance with the present invention, wherein the surgical scissors are shown in their open position;

FIG. 2 is a top view of the same pair of surgical scissors, wherein the surgical scissors are still shown in their open position;

FIG. 3 is a right side view of the right scissor blade member of the surgical scissors shown in FIGS. 1 and 2, wherein the scissor blade member is shown at an intermediate stage of manufacture when it is in a substantially straight configuration;

FIG. 4 is a top view of the same scissor blade member shown in FIG. 3;

FIG. 5 is a left side view of the same scissor blade member shown in FIG. 3;

FIG. 6 is a front end view of the same scissor blade member shown in FIG. 3;

DETAILED DESCRIPTION OF THE PREFERRED EMBODIMENT

Figure 7:
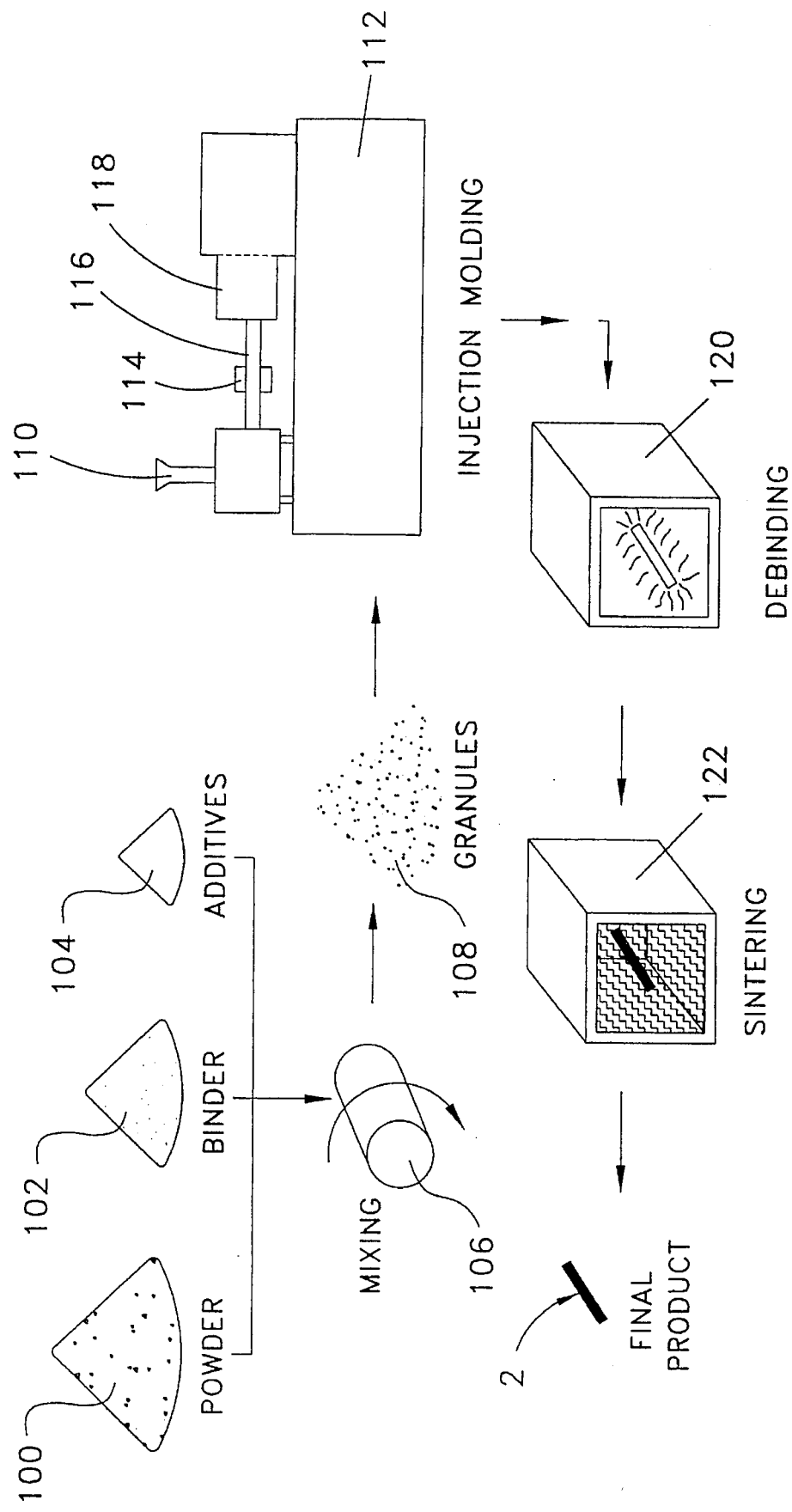
FIG. 7 is a schematic diagram of the various steps involved in a conventional powdered metal injection molding process.
Figure 8:
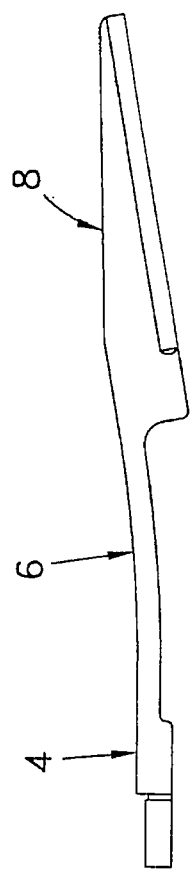
FIG. 8 is a right side view of the same scissor blade member shown in FIG. 3, except that the scissor blade member is shown at a later stage of manufacture when it is in a curved configuration.
Figure 9:
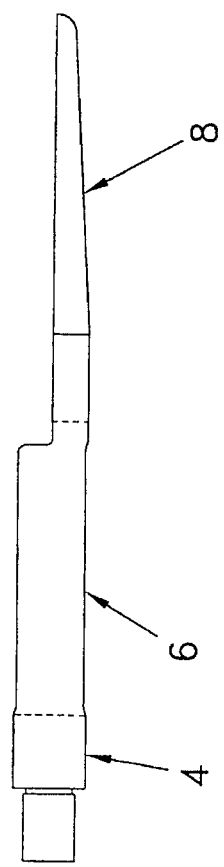
FIG. 9 is a top view of the same scissor blade member shown in FIG. 8.
Figure 10:
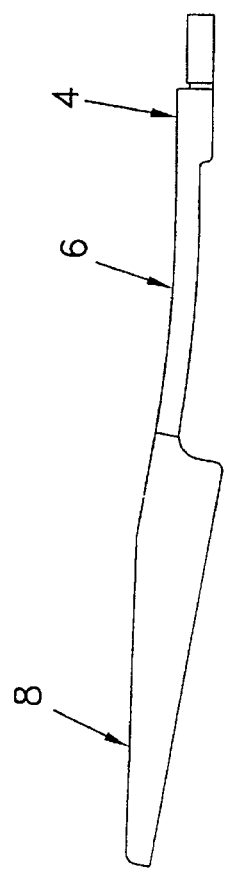
FIG. 10 is a left side view of the same scissor blade member shown in FIG. 8.

FIGS. 1 and 2 illustrate a particularly advantageous embodiment of the present invention, wherein two identical scissor blade members 2, formed by the method of the present invention, are fastened together so as to form a pair of surgical scissors. These surgical scissors are of the sort intended to be used in a scissor device of the type disclosed in the aforementioned U.S. Pat. No. 5,334,198, which patent is incorporated herein by reference.

Each scissor blade member 2 generally comprises a body portion 4 having a semi-circular cross-section, a spring arm portion 6 also having a semi-circular cross-section, and a blade portion 8.

Referring now to FIGS. 3–6, body portion 4 has an inner flat surface 10 and an outer semi-circular surface 12. Body portion 4 further includes a proximal section 14 having a peripheral groove 16. When two scissor blade members 2 are fastened together as shown in FIG. 1, the two proximal sections 14 and the two grooves 16 combine so as to form a first mount assembly adapted to engage a corresponding second mount assembly of the sort provided at the distal end of the scissor handle's elongated midsection. See, for example, the aforementioned U.S. Pat. No. 5,334,198, which discloses structure of the sort just described.

The blade member's spring arm portion 6 is formed integral with body portion 4 and extends from the distal end of body portion 4. Spring arm portion 6 has a semi-circular cross-section which is generally similar to that of body portion 4, except that its inner flat surface 18 is recessed somewhat relative to flat surface 10 of body portion 4, whereby spring arm portion 6 has a reduced thickness relative to body portion 4. The degree to which the spring arm's inner surface 18 is recessed relative to inner surface 10 may be varied somewhat as desired, in order to regulate the spring characteristics of spring arm portion 6.

Blade portion 8 extends from the distal end of spring arm portion 6 and is formed integral therewith. Blade portion 8 includes a transition section 20 and an edge section 22. The transition section 20 has a semi-circular cross-section and includes an inner surface region 24. Inner surface region 24 is oriented so that it extends nearly perpendicular to the spring arm's inner surface 18 and to the body portion's inner surface 10, as seen in FIGS. 5 and 6.

The blade's edge section 22 is formed integral with its transition section 20 and extends from the distal end thereof. Edge section 22 comprises an inner surface region 26 and an outer blade face portion 28. The edge section's inner surface region 26 is coplanar with the transition section's inner surface region 24, as seen in FIGS. 4 and 5. Blade face portion 28 (FIGS. 3 and 6) extends at an angle of between about 25 and about 60 degrees relative to inner surface region 26, intersecting inner surface region 26 along a linear shearing edge 30 (FIG. 6). In order to provide the required sharpness for surgical procedures, the width of shearing edge 30 must be less than or equal to about 0.002 inches. In practice, it can be determined whether this requirement has been met by examining shearing edge 30 under a conventional 10X magnifier; if no land is visible at this level of magnification, shearing edge 30 is properly formed.

In accordance with the present invention, the above-described scissor blade members 2 are manufactured by a novel application of conventional powdered metal injection molding techniques.

More particularly, powdered metal injection molding per se is well known in the art. It has been previously applied to manufacture a wide variety of parts, including wire and cable crimping tools, router bit bodies, cutting tools and other complex, close tolerance parts, as disclosed in the December 1988 issue of "AMERICAN MACHINIST" magazine, at pages 45–48. The present invention, however, is directed to the novel application of such powered metal injection molding techniques so as to form surgical scissor blades that have sharp, burr free shearing edges and improved spring characteristics.

FIG. 7 is a schematic representation of a conventional powdered metal injection molding system of the sort well known in the art. The process begins by combining metal powder 100 with a binder 102 and additives 104 in a mixer 106 so as to form a homogeneous granular mixture 108.

Mixture 108 preferably comprises approximately 80% (by weight) metal powder 100. As disclosed in "Powder Injection Molding of 17-4PH Stainless Steel" by H. Zhang and R. M. German, as published in "Powder Injection Molding Symposium 1992" at pages 219–227, 17-4PH stainless steel is a preferred metal for use in powdered metal injection molding. In the present invention, 17-4PH stainless steel has been found to be satisfactory for producing the desired scissor blades. Of course, other metals and metal alloys may also be used, such as 17-7PH stainless steel, 6Al-4 V titanium-aluminum alloy and, in the case of blades which are to be employed in bi-polar cauterizing scissors, aluminum. To achieve optimum results, metal powder 100 should have an average particle size of less than or equal to about 15 microns.

Mixture 108 preferably comprises approximately 20% (by weight) binder 102 and additives 104.

Binder 102 serves to promote moldability when the mixture is introduced into a conventional molding machine. Binder 102 acts as a viscous carrier, when heated under pressure, to help transport the metal powder 100 through the molding machine's screw feed and into the mold cavity. Binder 102 is of the sort commonly used in metal injection molding and well known to those skilled in the art. Typically, binder 102 comprises a combination of paraffin wax, polypropylene and carnauba wax.

Additives 104 serve to improve the viscosity and moldability of the mixture, as well as to reduce corrosion of the mold tool. Additives 104 are also of the sort well known in the art and typically include stearic acid and various plasticisers.

The metal powder 100, binder 102 and additives 104 are mixed together to a uniform consistency in a conventional mixer 106 so as to yield the above-described mixture 108. Once thoroughly mixed, the mixture 108 is placed in the hopper 110 of a conventional injection molding machine 112. A conventional band heater 114 melts the binder 102 and additives 104. A screw feed 116 transports the mixture 108 into the mold 118 under pressure. Once mixture 108 has been fully injected and packed into the mold cavity, the mold is held clamped for a 15 to 20 second cool time. The molded parts (frequently referred to as "green" blades at this point due to their unfinished state) are then ejected from the cavity and allowed to fall onto a soft, shock absorbing material for subsequent processing. It is to be appreciated that by appropriately forming the interior cavity of mold 118, the molded part will include the sharp shearing edge required for cutting tissue. Furthermore, the molded part will emerge from the mold with its sharp shearing edge completely free from burrs and the like.

In this respect it is also to be appreciated that the substantial pressure generated by screw feed 116 promotes very close "packing" of the metal particles in the mold cavity, so as to result in improved densities in the finished part. In fact, better than 99% density (as compared to a scissor blade member formed using a conventional machined technique) has been achieved with this method, thereby yielding a sharp, burrless shearing edge on the blade.

It is also to be appreciated that a conventional mold tool 118 is utilized in forming the scissor blade members. Typically, mold tool 118 is a single cavity design, however, multiple cavity mold tools may also be employed with equal benefit. The mold tool cavity is preferably produced through conventional EDM (electric discharge machining) methods of the sort well known to those skilled in the art. Insert mold cavities may also be used with nearly equivalent results.

Mold tool 118 is similar in most respects to a conventional mold of the sort used in plastics injection molding. A significant difference between a mold used in plastics injection molding and a mold used in powdered metal injection molding, however, is the lack of vents in the mold tool cavities for powdered metal injection molding. This is due to the tendency of the viscous, pressurized powdered metal to exhibit flashing when it is injected and packed into a mold at the high density required to form acceptable blade members. Also, as a result of this tendency to exhibit flashing, tighter tolerances are required on the mold cavity dimensions for powdered metal molding.

If desired, the green blade may be stored for some period of time after it is removed from mold 118 and before its processing is completed. More typically, however, the green blade is transferred directly to a binder removal chamber 120 for debinderizing. Care should be taken at this point in handling the green blade due to its extreme brittleness. Rough handling may result in a cracked or broken blade. The temperature of chamber 120 is then elevated, under vacuum, to volatilize and remove the binder 102 and additives 104 from the blade. A typical process for debinderizing comprises holding the blade at 90° C. for 12 hours, followed by 100° C. for an additional 12 hours, then holding the blade at 130° C. for an additional 12 hours, and finally keeping the blade at 140° C. for a final 12 hours. As a result of this debinderizing step, approximately 65% of the binder 102 and additives 104 are removed from the blade. The residual binder 102 and additives 104 are removed from the blade during a pre-sintering temperature warmup. It is to be appreciated that the foregoing removal of binder 102 and additives 104 from the molded blade does not degrade the sharp, burr-free shearing edge imparted to the blade during molding.

Once the blade has been debinderized, it is ready for sintering in chamber 122. Typically, a part molded from 17-4PH stainless steel is sintered at a temperature of from 1250° to 1340° C. for one hour, in a hydrogen atmosphere. This causes the metal particles to strongly adhere to one another so as to give the molded part its structural integrity. At the end of sintering, the blade is allowed to furnace cool. As a result of sintering, one can expect a 10–30% shrinkage from the green state to the sintered final form of the blade. Shrinkage in the present invention has been about 20%. It should be noted that powdered stainless steel materials exhibiting shrink rates on the order of only about 4% have recently become commercially available. It is anticipated that such materials will likewise be effective in manufacturing the scissor blades of the present invention. It is to be appreciated that the molded blade emerges from the sintering process with its shearing edge still very sharp and completely burr free.

At this point additional forming or machining operations may be performed on the sintered part. For example, in the preferred embodiment of the invention, the straight scissor blade of FIGS. 3–6 is bent about a radius so that a slight curvature is imparted to the blade, as shown in FIGS. 1, 2 and 8–10. This curvature acts to increase the shearing action of the scissor blades 2 when they are assembled together in the form shown in FIGS. 1 and 2. It is to be understood, however, that this curvature can also be applied, with equal effect, in the mold by means of utilizing an appropriately curved cavity, if desired.

The scissor blade is then heat treated to temper and harden the blade. Typically, heat treatment is conducted in a hydrogen atmosphere, at 480° C. for approximately one hour. In the preferred embodiment, a hardness of H-900 (equivalent to a hardness of 40–44 on the Rockwell "C" scale) is required to provide the requisite durability in the blade's shearing surfaces. Spring properties of better than approximately 95% have been achieved in the finished blade after tempering. These spring properties are superior to the spring properties of conventional scissor blades. The finished blade is then allowed to air cool. The foregoing process yields a finished sintered powder metal blade which has a very sharp shearing edge which is completely burr free, and which has superior spring properties to conventional scissor blades.

Alternative Embodiments

Although the blade design discussed above constitutes a preferred embodiment of the invention, other designs may also be produced by the method of the present invention and are considered to be within its scope. For example, scissor blades having hooked or serrated blade sections can be manufactured by the method of the present invention. Furthermore, miniature versions of the aforementioned scissor blades are also easily manufactured with appropriately dimensioned mold cavities.

Also, the method of the present invention is not limited to the manufacture of scissor blades used in endoscopic surgical procedures. For example, various scissors, forceps, tweezers, etc. of conventional design can also be manufactured by the present method, at significant cost savings. Such instruments can also be formed in miniature by the method of the present invention.

These and other modifications will be obvious to those skilled in the art and are considered to be within the scope of the present invention.

Advantages Of The Invention

Numerous advantages are obtained through the use of the present invention.

First, it allows a surgical scissor blade to be manufactured which is extremely sharp and durable.

Second, no burr is produced on the shearing edge of the scissor blade during any portion of the manufacturing process. Thus, the scissor blade does not need to be deburred as part of the manufacturing process.

Third, custom shaped blades are easily and economically manufactured by the method of the present invention.

Fourth, the present invention significantly reduces the scrap rate associated with the production of surgical scissor blades.

Fifth, various exotic metals and metal alloys are easily incorporated into the disclosed method for producing surgical scissor blades.

Sixth, the method of the present invention can be used to produce medical instruments at a significantly lower cost than conventional fabrication methods.

Seventh, scissor blades exhibiting enhanced spring properties and fatigue strength are produced.

What is claimed is:

1. A surgical scissor blade comprising a sharp shearing edge, said shearing edge and a remainder of said blade comprising one unitary and integral molded body composed of an injection molded and hydrogen sintered powdered metal selected from a group consisting of stainless steel, titanium-aluminum alloy, and aluminum, of particle size of about 15 microns, said blade being shrunken from a pre-sintered configuration to a smaller sintered configuration, said blade shearing edge formed by said molding and said sintering being devoid of burrs.

2. A surgical scissor blade comprising shearing means for shearing tissue, said shearing means being a portion of an injection molded unitary body, said body composed of powdered metal selected from a group consisting of stainless steel, titanium-aluminum alloy, and aluminum, of particle size of about 15 microns, a binder selected from a group consisting of at least one of paraffin wax, polypropylene, and carnauba wax, and additives including at least one of stearic acid and a plasticiser, said shearing means comprising a shearing edge formed by the injection molding and devoid of burrs.

3. A unitary surgical scissor blade comprising a body portion having inner and outer surfaces and including engagement means at a proximal end thereof;

a spring arm portion integral with and extending from a distal end of said body portion, said spring arm portion including inner and outer surfaces and having a cross-section less than said body portion; and a blade portion integral with and extending from a distal end of said spring arm portion, said blade portion comprising an inner surface and a blade face in spaced apart, confronting relationship, said inner surface and said blade face meeting in a linearly-extending shearing edge;

wherein said unitary scissor blade is composed of a sintered powdered metal and said spring arm portion of said unitary blade provides all of a spring bias exhibited by said blade when in combination with a second similar blade to form a scissors assembly, such that said unitary blade is devoid of attachment to and engagement with any discrete spring member other than said second similar blade.

4. A surgical scissor blade according to claim 3 wherein said shearing edge is free from burrs.

5. A surgical scissor blade according to claim 3 wherein said inner surface of said body portion is adapted to be attached to an identical surface of another scissor blade so as to form a whole scissors.

6. A surgical scissor blade according to claim 3 wherein said blade portion is curved about at least one axis thereof.

7. A surgical scissor blade according to claim 3 wherein said blade portion is serrated.

8. A surgical scissor blade according to claim 3 wherein said blade portion is hooked.

9. A surgical scissor blade according to claim 3 wherein said scissor blade comprises 17-4PH stainless steel.

10. A surgical scissor blade according to claim 3 wherein said powdered metal is selected from the group consisting of 17-4PH stainless steel, 17-7PH stainless steel, 6A1-4V titanium aluminum, and aluminum.

11. A surgical scissor blade according to claim 3 wherein said shearing edge is less than about 0.002 inches wide.

* * * * *